United States Patent [19]

Casillan

[11] Patent Number: 4,999,200
[45] Date of Patent: Mar. 12, 1991

[54] PSYLLIUM TABLET COMPOSITION, METHOD OF MANUFACTURE AND METHOD OF USE

[75] Inventor: Angel Casillan, Overland Park, Kans.

[73] Assignee: Marion Laboratories, Kansas City, Mich.

[21] Appl. No.: 130,021

[22] Filed: Dec. 9, 1987

[51] Int. Cl.$^5$ .................... A61K 9/36; A61K 9/20; A61K 35/78
[52] U.S. Cl. .................... 424/480; 424/464; 424/465; 424/474; 424/195.1; 514/892
[58] Field of Search .................... 424/195.1, 464, 465, 424/474, 480; 514/892

[56] References Cited

U.S. PATENT DOCUMENTS

| | | | |
|---|---|---|---|
| 3,922,339 | 11/1975 | Shear | 424/498 |
| 4,321,263 | 3/1982 | Powell et al. | 424/195.1 |
| 4,511,561 | 4/1985 | Madaus et al. | 424/195.1 |
| 4,551,331 | 11/1985 | Rudin | 424/195.1 |
| 4,588,589 | 5/1986 | Sheth et al. | 424/195.1 |
| 4,603,126 | 7/1986 | Yamatsu et al. | 514/739 X |
| 4,639,367 | 1/1987 | Mackles | 514/945 X |
| 4,666,716 | 5/1987 | Sheth et al. | 424/195.1 |
| 4,683,256 | 7/1987 | Porter et al. | 424/494 X |
| 4,689,229 | 8/1987 | Banik | 424/195.1 |

Primary Examiner—John W. Rollins
Assistant Examiner—W. Catchpole
Attorney, Agent, or Firm—Robert S. Beiser

[57] ABSTRACT

A psyllium composition in tablet form is provided having a wetting agent, a disintegrant and a binding agent. In one embodiment, the wetting agent is polysorbate 80, the binding agent is polyvinyl pyrrolidone and the dry binding agent and disintegrant is microcrystalline cellulose. Calcium carbonate may also be added to serve as a disintegrant in HCL. The tablets are manufactured by mixing the psyllium powder with a solution of povidone and polysorbate 80. Microcrystalline cellulose may be added either during or after granulation. After mixing, the composition is compressed into tablet form. The mixing of the ingredients in specific quantities allows a tablet to be manufactured that is both resistant to fracture and at the same time disintegrates easily and quickly in the gastrointestinal tract of the patient.

10 Claims, 1 Drawing Sheet

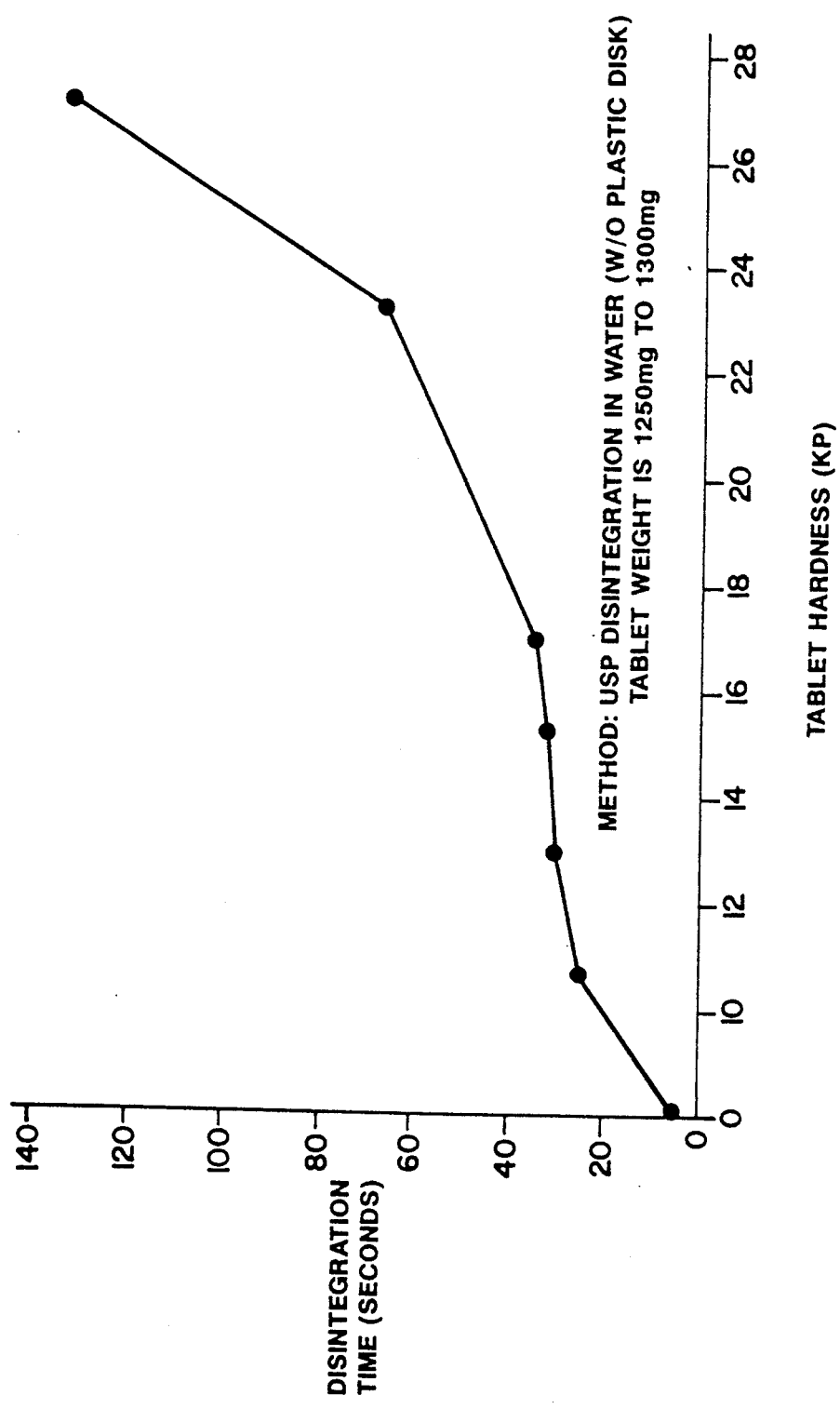

PSYLLIUM TABLET COMPOSITION, METHOD OF MANUFACTURE AND METHOD OF USE

BACKGROUND OF THE INVENTION

Powdered husks of the psyllium seed are a common and effective bulk laxative. The hydrophilic properties of this natural fibrous laxative cause ingested doses to absorb large amounts of water, thus producing bulk and normalizing regularity through proper stool formation.

A single, normal adult dose of psyllium bulk laxative is about 3 grams of psyllium powder, dispersed by the user in water or in an aqueous beverage. However, powdered psyllium has very poor wetting capabilities and therefore must be vigorously mixed with aqueous fluids to produce a palatable dispersion.

Psyllium powder resists wetting in water or aqueous beverages because of its fine particle size and the inability of water to penetrate the powder mass due to fast surface hydration and swelling. Vigorous agitation of the psyllium powder in water results in a lumpy dispersion. The lumps, although wetted on their outer surface, contain dry undispersed powder on the inside. Fluid penetration must therefore precede hydration in order to accomplish instant wettability and dispersability.

A number of attempts have been made in the past to improve the usability of psyllium. U.S. Pat. No. 4,321,263, for example, describes coating granulated psyllium particles with an alcoholic solution of either polyethylene glycol or polyvinyl pyrrolidone and granulating the thus coated particles.

U.S. Pat. No. 4,588,589 teaches an antidiarrheal composition comprising bismuth subsalicylate and a polymeric hydroabsorptive agent selected from psyllium and glucomannan. The compositions may be prepared in a variety of forms which can be taken orally.

U.S. Pat. No. 4,666,716 is also directed to an antidiarrheal composition in which nonsteroidal anti-inflammatory drugs are combined with a polymeric hydroabsorptive agent such a psyllium in a variety of forms.

U.S. Pat. No. 3,922,339 describes coating of a medicant with a psyllium film.

U.S. Pat. No. 4,639,367 teaches a psyllium bulk laxative foam.

Currently, psyllium products are marketed in powder mixtures and chewable dosage form. As noted above, use of psyllium in a powdered form as a bulk laxative has posed some difficulty in mixing of the psyllium with water. As a result, a tablet dosage form for bulk laxative would be preferred. However, rapid and complete disintegration of the tablet is critical to the proper performance of psyllium. The tablet breakup and particle deaggregation must be maximized in order to improve the capability of psyllium to absorb and retain the moisture and act as a bulk providing medium.

A problem in making psyllium bulk laxative in tablet form is that psyllium is not compressible; it is very elastic with very minimal plastic deformation. In addition, compressed tablets must be able to withstand the process involved in tablet coating and packaging without crumbling. At the same time, improperly formulated tablets will not disintegrate into particles, thereby inhibiting the swelling of psyllium into gel.

Accordingly, it is an object of the present invention to provide a psyllium tablet that is sufficiently compressable to be manufactured, disintegrates easily in water and yet is not fragile during shipment.

SUMMARY OF THE DISCLOSURE

It has been found that an improved bulk laxative composition in tablet form may be provided by combining psyllium, a wetting agent, a disintegrant and a binding agent, all in specific quantities selected so as to exhibit the desired properties. In particular, in a preferred embodiment, the composition includes psyllium powder, polysorbate 80 as the wetting agent, polyvinyl pyrollidone as the binding agent and microcrystalline cellulose as the binding agent and as the disintegrant. It should be noted that polysorbate 80 is an oleate ester of sorbitol and its anhydride condensed with polymers of ethylene oxide consisting of approximately 20 oxyethylene units. Calcium carbonate may also be added to facilitate disintegration in stomach acid.

In addition to the novel psyllium composition, the invention further includes a method of preparing a bulk laxative composition in tablet form. The method includes the steps of granulating psyllium powder with povidone-polysorbate solution in water. The granulated mixture is then dried. The microcrystalline cellulose may be added during wet granulation or during the dry mixing before tablet compression. The material is then compressed using conventional tablet forming equipment. The resulting tablets may then be coated with hydroxypropyl methylcellulose film.

The invention further includes a method of treating constipation in humans. The method comprises the step of administering to the patient a bulk laxative tablet comprising a combination of psyllium, a wetting agent, a disintegrant and a binding agent, the composition being formulated to disintegrate rapidly and thoroughly in the patient's gastrointestinal tract.

BRIEF DESCRIPTION OF THE DRAWING

FIG. 1 is a chart illustrating the disintegration rate of psyllium tablets in water.

DETAILED DESCRIPTION OF THE PREFERRED EMBODIMENT

The present invention comprises a bulk laxative in tablet form containing the combination of psyllium, a wetting agent, a disintegrant and a binding agent. Calcium carbonate may also be added as a disintegrant in HCL.

More particularly, in a preferred embodiment the psyllium comprises approximately 50 parts, the calcium carbonate comprises approximately 2.5 parts and the microcrystalline cellulose comprises approximately 100 parts. The weight ratio of microcrystalline cellulose to psyllium is about 2:1. The weight ratio of psyllium to calcium carbonate is about 20:1.

Although calcium carbonate is added as an aid to disintegration in HCL, it is not essential to the invention. In larger quantities, calcium carbonate may also be added as an excipient; an inert diluent. Although calcium carbonate is a preferred excipient, other excipients such as magnesium carbonate, calcium phosphate, calcium sulphate, lactose, cellulose, microcrystalline cellulose, starch, modified starch, dextrose, sucrose, mannitol and sorbitol may be utilized.

Although polyvinyl pyrrolidone is preferred as a binding agent, it is believed that cellulose ethers such as sodium carboxymethylcellulose, methyl cellulose, hydroxypropyl cellulose, hydroxypropylmethyl cellulose, hydroxy ethyl cellulose and ethyl cellulose, natural gums such as acacia, tragacanth, pectin, guar and karaya, gelatin, alginates, starch, modified starch, polyethylene glycol, sugars such as sucrose, sorbitol and glucose, corn syrups, polyvinyl alcohols, polyacrylamides, or polyvinyloxoazolidone could be used. A preferred disintegrant is polysorbate 80 and microcrystalline cellulose. Polysorbate 80 is a wetting agent and also aids as a disintegrant. Microcrystalline cellulose is an excipient which may also act as a dry binding agent and as a disintegrant. It is believed that other disintegrants such as sodium starch glycollate, cross-linked carboxymethyl cellulose, ion exchange resins, starch, modified starches, cellulose derivatives, alginates, alginic acid or clays may be used.

The tablets may be coated with hydroxypropyl methylcellulose film, or other binding agents in film form to improve handling properties during packaging and shipment. The finished coated tablets disintegrate easily in water or 0.1N HCL.

Psyllium customarily has been given in powdered form in a dosage of 750 mg to 900 mg. In the present case, a daily dosage of 2.4 to 3.6 grams is preferred. The means of dosage are preferably 4 tablets of from 600 to 900 mg psyllium apiece.

In a preferred embodiment, the polyvinyl pyrrolidone comprises approximately 10% of the solution used to formulate the tablets. Similarly, the polysorbate 80 comprises approximately 1% of the solution.

As may be seen in the following examples, the use of psyllium powder in combination with improper quantity of microcrystalline cellulose, and povidone does not produce an acceptable psyllium bulk laxative in tablet form. Similarly, the combination of psyllium, dextrose monohydrate and povidone also does not produce a suitable product. It is only the combination of psyllium and a wetting agent, a disintegrant and a binding agent such as polysorbate 80; povidone and/or microcrystalline cellulose that results in a tablet that is suitable for commercial production and which disintegrates easily in the gastrointestinal tract of the patient. Accordingly, a novel, easily used and low cost laxative is thereby provided.

EXAMPLE 1

Psyllium Powder—50 parts
Microcrystalline Cellulose NF—50 parts
Method: Dry mixed powders do not compress into acceptable tablets.

EXAMPLE 2

Psyllium Powder—80 parts
Microcrystalline Cellulose NF—20 parts
Povidone USP q.s. as Binder
Method: Mixed powders of Psyllium and Microcrystalline Cellulose are granulated with Povidone solution in water and then dried. Compressed tablets are soft and do not disintegrate into particles in water. A film or gel is formed on the tablet surface.

EXAMPLE 3

Psyllium Powder—80 parts
Dextrose Monohydrate—20 parts
Povidone USP q.s. as Binder
Method: Mixed powders of Psyllium and Dextrose Monohydrate are granulated with Povidone USP solution in water and then dried. Compressed tablets are soft and do not disintegrate in water.

EXAMPLE 4

Psyllium Powder—50 parts
Dextrose Monohydrate—50 parts
Povidone USP q.s. as Binder
Method: Mixed powders of Psyllium and Dextrose Monohydrate are granulated with Povidone USP solution in water and then dried. Compressed tablets are hard but do not disintegrate in water.

EXAMPLE 5

Psyllium Powder—50 parts
Calcium Carbonate* USP—2.5 parts (or q.s.)

*Calcium Carbonate is added to enhance the rapid disintegration of the tablet in 0.1N HCl. Polysorbate 80 promotes the wetting of the powders during disintegration in fluids.

Polysorbate 80, NF—q.s.
Povidone, USP—q.s.
Microcrystalline Cellulose NF—q.s. 100 parts
Method: The powders are granulated with the Povidone-Polysorbate 80 solution in water and then dried (a portion or the entire amount of the Microcrystalline Cellulose may be added during wet granulation or during the dry mixing before tablet compression). Compressed tablets are coated with Hydroxypropyl Methylcellulose film. The finished coated tablets disintegrate easily in water, 0.1N HCl or in pH 8.0 buffer solution.

EXAMPLE 6

Purpose: To determine how variations in hardness through differences in compression effect disintegration of the psyllium tablets in water.

Procedure: Tablets with varying tablet hardness were prepared using Stokes F-Press PD #20. All tablets were formulated using the mixture set forth in Example 5 (sub batches A, B, C, D, J, K). Tooling=0.745"×3125" capsule shape. For Lot #E, F, G, H, I, tablets were prepared manually by turning the fly-wheel to provide the required dwell time for the manufacturing of hard tablets. The tablet hardness was determined by using the Key hardness tester PD #408.

| Results | | | | | | | | | | | |
|---|---|---|---|---|---|---|---|---|---|---|---|
| A | | B | | C | | D | | J | | K | |
| Weight | Kp | Weight | Kp | Weight | Kp | Weight | Kp | Weight | Kp | Weight | Kp |
| 1.290 | 6.5 | 1.300 | 8.5 | 1.300 | 8.4 | 1.290 | 10.3 | 1.290 | 11.4 | 1.250 | 12.5 |
| 1.290 | 6.6 | 1.260 | 8.6 | 1.300 | 10.0 | 1.290 | 10.9 | 1.280 | 12.1 | 1.220 | 12.1 |
| 1.310 | 6.3 | 1.300 | 8.1 | 1.300 | 9.9 | 1.290 | 11.4 | 1.280 | 10.6 | 1.250 | 13.5 |
| 1.310 | 6.9 | 1.310 | 7.0 | 1.300 | 8.5 | 1.290 | 11.1 | 1.290 | 10.2 | 1.250 | 13.3 |
| 1.310 | 6.3 | 1.310 | 7.3 | 1.300 | 9.8 | 1.290 | 11.1 | 1.280 | 10.8 | 1.270 | 13.3 |
| 1.310 | 6.5 | 1.310 | 8.7 | 1.300 | 9.9 | 1.290 | 9.5 | 1.290 | 12.5 | 1.270 | 13.4 |
| 1.310 | 7.0 | 1.310 | 8.6 | 1.310 | 9.9 | 1.290 | 10.1 | 1.290 | 9.9 | 1.230 | 13.3 |
| 1.310 | 6.6 | 1.300 | 8.2 | 1.310 | 9.8 | 1.290 | 10.8 | 1.290 | 10.3 | 1.230 | 13.7 |
| 1.310 | 6.6 | 1.310 | 8.1 | 1.300 | 8.5 | 1.300 | 10.4 | 1.290 | 11.7 | 1.230 | 12.8 |
| 1.320 | 6.2 | 1.310 | 8.3 | 1.310 | 9.7 | 1.310 | 11.4 | 1.280 | 11.7 | 1.220 | 11.7 |
| $\bar{x}$ = 1.31 g | $\bar{x}$ = | $\bar{x}$ = 1.30 g | $\bar{x}$ = | $\bar{x}$ = 1.30 g | $\bar{x}$ = | $\bar{x}$ = 1.290 g | $\bar{x}$ = | $\bar{x}$ = 1.290 g | $\bar{x}$ = | $\bar{x}$ = 1.240 g | $\bar{x}$ = |

-continued

| Results | | | | | |
|---|---|---|---|---|---|
| 6.6 | 8.1 | 9.4 | 10.7 | 11.1 | 13.0 |

E, F, G, H, I (Manually Turned)

| E | | F | | G | | H | | I | |
|---|---|---|---|---|---|---|---|---|---|
| Weight | Kp | Weight | Kp | Weight | Kp | Weight | Kp | Weight | Kp |
| 1.280 | 19.6 | 1.280 | 17.4 | 1.250 | 24.5 | 1.310 | 19.6 | 1.230 | 26.4 |
| 1.290 | 15.6 | 1.280 | 15.9 | 1.240 | 24.6 | 1.320 | 16.5 | 1.260 | 24.8 |
| 1.330 |  | 1.250 | 13.2 | 1.250 | 22.0 | 1.330 | 22.9 | 1.250 | 29.6 |
| 1.290 | 16.9 | 1.260 | 14.5 | 1.260 | 21.9 | 1.320 | 19.6 | 1.260 | 26.9 |
| 1.290 | 17.5 | 1.280 | 15.6 | 1.260 | 23.2 | 1.320 | 19.9 | 1.210 | 27.1 |
| 1.280 | 15.3 |  |  |  |  | 1.300 | 19.7 |  |  |
| 1.290 | 16.8 |  |  |  |  |  |  |  |  |
| $\bar{x}$ = 1.290 g | $\bar{x}$ = 17.0 | $\bar{x}$ = 1.290 g | $\bar{x}$ = 15.3 | $\bar{x}$ = 1.250 g | $\bar{x}$ = 23.2 | $\bar{x}$ = 1.320 g | $\bar{x}$ = 19.7 | $\bar{x}$ = 1.250 g | $\bar{x}$ = 27.0 g |

NOTE
Tablet weights were rounded to the nearest 0 zero.

DISINTEGRATION TESTING

Method: Granulations of psyllium were compressed into tablets using the model F stokes single punch tooling 0.745″×0.3125″ capsule shape (refer to PD—13-18-85). Tablets were subjected to disintegration using the USP methods, without the use of plastic disk. Fluid used was water at 37 degrees C.±2 degrees C.

RESULTS

| Lot # of Tablets | Tab Wt. [Average] | Tab Hardness [Average] | Disintegration Time in H₂O |
|---|---|---|---|
| A | 1300 mg | 8.1 Kp | 5 secs |
| D | 1290 mg | 10.7 Kp | 25 secs |
| K | 1240 mg | 13.0 Kp | 30 secs |
| F | 1270 mg | 15.3 Kp | 32 secs |
| E | 1290 mg | 17.0 Kp | 35 secs |
| G | 1250 mg | 23.2 Kp | 67 secs |
| I | 1250 mg | 27.0 Kp | 133 secs |

The tablet hardness was determined using a Key hardness tester.

A graphic illustration of the above results is shown in FIG. 1.

Conclusions: Variations in hardness of from 8.1 Kp to 27.0 Kp using a preferred formulation (50 parts psyllim, calcium carbonate Q.S., polysorbate 80 Q.S., povidone Q.S. and Q.S 100 parts microcrystalline cellulose) were effected by varying the compression of the tablets. The resulting tablets had a disintegration time in water of from 5 seconds to 133 seconds. However, since a disintegration time of 15 minutes is acceptable for human use, all of the tablets tested are acceptable.

Thus a bulk laxative composition in tablet form is provided comprising psyllium, polysorbate 80, polyvinyl pyrrolidone and microcrystalline cellulose. Calcium carbonate may also be added as a disintegrant in stomach acid. A method of manufacturing the aforesaid composition and of treating constipation in humans is also disclosed.

What is claimed is:

1. A bulk laxative composition in tablet form consisting essentially of:
   50 parts of psyllium powder ±10;
   1.5 parts of a wetting agent ±1.0;
   100 parts of a binding agent ±10; and
   2.5 parts of a disintegrating agent ±0.5, to provide a tablet which resists fracture in commercial production but disintegrates easily in water or stomach acid.

2. A bulk laxative composition in tablet form consisting essentially of:
   50 parts of psyllium powder ±10;
   1.5 parts of polysorbate 80 ±1.0;
   15 parts of polyvinyl pyrrolidone ±1.0; and
   100 parts of microcrystalline cellulose ±10.

3. The composition of claim 2 and further including calcium carbonate as a disintegrant in stomach acid.

4. The composition of claim 1 wherein said tablets are coated with an hydroxypropyl methylcellulose film.

5. A method of treating constipation in a patient comprising:
   administering to the patient an effective amount of a bulk laxative in tablet form consisting essentially of, the composition of 50 parts of psyllium powder ±10, 1.5 parts of polysorbate 80 ±1.0, 100 parts of microcrystalline cellulose ±10, 2.5 parts of calcium carbonate ±0.5 and 15 parts of polyvinyl pyrrolidone ±1.0, said tablet being formulated so as to disintegrate rapidly and thoroughly in the patient's gastrointestinal tract.

6. The method of claim 5 wherein the total daily dosage of said psyllium is approximately 2.4 to 3.6 grams.

7. The method of claim 5 and further comprising:
   administering one to four of said tablets to the patient wherein each tablet has 600-900 mg psyllium.

8. A method of preparing a bulk laxative composition in tablet form, said method comprising the steps of:
   granulating psyllium powder with povidone-polysorbate solution in water;
   adding microcrystalline cellulose;
   drying the mixture of said granulated psyllium powder with povidone-polysorbate solution in water and said microcrystalline cellulose; and
   compressing the resulting composition into tablets.

9. The method of claim 8, wherein said tablets are coated with hydroxypropyl methylcellulose.

10. The method of claim 8 and further comprising the steps of:
    adding a portion of said microcrystalline cellulose during wet granulation.

* * * * *